(12) United States Patent
Ellis et al.

(10) Patent No.: US 6,654,736 B1
(45) Date of Patent: Nov. 25, 2003

(54) CHEMICAL INFORMATION SYSTEMS

(75) Inventors: William Y. Ellis, Laurel, MD (US); John D. Notsch, Rockville, MD (US); Patrick B. McGreevy, Glencoe, CA (US)

(73) Assignee: The United States of America as represented by the Secretary of the Army, Washington, DC (US)

( * ) Notice: Subject to any disclaimer, the term of this patent is extended or adjusted under 35 U.S.C. 154(b) by 0 days.

(21) Appl. No.: 09/436,226

(22) Filed: Nov. 9, 1999

(Under 37 CFR 1.47)

Related U.S. Application Data

(60) Provisional application No. 60/107,690, filed on Nov. 9, 1998.

(51) Int. Cl.⁷ .............................................. G06F 17/30
(52) U.S. Cl. ........................... 707/3; 707/10; 707/104.1
(58) Field of Search ...................... 707/1–3, 100–104.1, 707/9–10; 704/9; 702/27

(56) References Cited

U.S. PATENT DOCUMENTS

| | | | | |
|---|---|---|---|---|
| 4,642,762 A | * | 2/1987 | Fisanick | 707/104.1 |
| 4,811,217 A | * | 3/1989 | Tokizane et al. | 707/3 |
| 5,418,944 A | * | 5/1995 | DiPace et al. | 702/27 |
| 5,577,239 A | * | 11/1996 | Moore et al. | 702/27 |
| 5,701,453 A | | 12/1997 | Maloney et al. | 707/2 |
| 5,920,871 A | | 7/1999 | Macri et al. | 707/104 |
| 5,950,192 A | * | 9/1999 | Moore et al. | 702/27 |

OTHER PUBLICATIONS

Army Research Office—Washington, "Integration of Text, Image, and Chemistry Databases on GUI Clients Designed for Drug Discovery and Development," Army SBIR Phase I Abstract Topic No. A96–131printout from www.aro.ncren-.net/arowash/rt/A9620250.htm dated Nov. 5, 1998.

DataAspects Corporation, "CIS Application Help," printout from file:///cl/daspects/cache/gaphelp.htm dated Nov., 9, 1999.

Daylight CIS, Inc., "Daylight Documentation," printout from www.daylight.com/dayhtml/doc/ dated Nov. 9, 1999.

Daylight CIS, Inc., "MUG '97—Presentations by Speaker," printout from www.daylight.com/meetings/mug97/presenters.html dated Nov. 9, 1999.

Daylight CIS, Inc., "MUG '99—Presentations by Speaker," printout from www.daylight.com/meetings/mug99/presenters.html dated Nov. 9, 1999.

Daylight CIS, Inc., "Daylight Published URLs," printout from www.daylight.com/dayhtml/published.html dated Nov. 9, 1999.

Feldman et al., "An Interactive Substructure Search System," Journal of Chemical Information and Computer Sciences, 1977, vol. 17, No. 3, pp. 157–163, American Chemical Society, Washington, D.C.

(List continued on next page.)

*Primary Examiner*—John Breene
*Assistant Examiner*—Mohammad Ali
(74) *Attorney, Agent, or Firm*—Elizabeth Arwine; Charles H. Harris

(57) ABSTRACT

A chemical information system having a graphical user interface that allows manipulation of multiple databases having related material and information. The system includes a server and multiple workstations communicating with the server. The databases reside on the server, which may include multiple servers.

10 Claims, 13 Drawing Sheets

OTHER PUBLICATIONS

Jacobus et al., "Experience with the Mechanized Chemical and Biological Information Retrieval System," Journal of Chemical Documentation, 1970, vol. 10, No. 2, pp. 135–140, American Chemical Society, Easton, PA.

Heller et al., "A Computer–Based Chemical Information System," Science, Jan. 21, 1977, vol. 195, No. 4275, pp. 253–259.

Heller et al., "An Experimental Computerized CBAC Search Project," Journal of Chemical Documentation, 1971, vol. 11, pp. 248–252, printed from www.hellers.com/steve/resume/p9.html on Dec. 3, 1998.

Heller et al., "Chemical Substructure Search Software for Personal Computers," Chemistry International, 1990, vol. 12, No. 3, pp. 89–94.

Heller et al., "The NIH/EPA Chemical Information System," ACS Symposium Series #84, 1978, chapter 10, pp. 144–167, American Chemical Society, Washington, D.C.

McGill et al., "A Computer–Based Toxicology Search System," Journal of Environmental Pathology and Toxicology, Nov.–Dec. 1978, vol. 2, No. 2, pp. 539–551, Pathotox Publishers, Inc.

Milne et al., "The NIH/EPA Chemical Information Systems," ACS Symposium Series #54, 1997, chapter 3, pp. 26–45, American Chemical Society, Washington, D.C.

Milne et al., "The NIH–EPA Chemical Information System," Proceedings of the ASIS $8^{th}$ Mid–year Spring Meeting, 1979, printed from www.hellers.com/steve/resume/p65.html on Dec. 2, 1998.

Milne et al., "The NIH–EPA Structure and Nomenclature Search System," Journal of Chemical Information and Computer Sciences, 1978, vol. 18, No. 4, pp. 181–186, American Chemical Society, Washington, D.C.

Milne et al., "The NIH/EPA Chemical Information System," Journal of Chemical Information and Computer Sciences, 1980, vol. 20, No. 4, pp. 204–211, American Chemical Society, Washington, D.C.

S.R. Heller, "The Chemical Substructure Searching on a PC," Proceedings of $11^{th}$ International Online Meeting, Dec. 8–10, 1987, pp. 25–32, Learned Information Ltd, Oxford, England.

S.R. Heller, "Structure Searching Systems," Proceedings of the $7^{th}$ International Online Meeting, Dec. 6–8, 1983, pp. 81–89, Learned Information Ltd., Oxford, England.

Stephen R. Heller, "The NIH/EPA Chemical Information System," Journal of Information Processing and Management, 1984, vol. 27, pp. 19–31, printed from www.hellers.com/steve/resume/p94fl.gif et seq on Dec. 3, 1998.

Stephen R. Heller, "The Chemical Information Systems and Spectral Databases," Journal of Chemical Information and Computer Sciences, 1985, vol. 25, No. 3, pp. 224–231, American Chemical Society, Washington, D.C.

Stephen R. Heller, "New Access to Data from the Beilstein Institute: Beilstein Online and SANDRA," paper printed from www.hellers.com/steve/resume/p102.html et seq, on Dec. 3, 1998.

Roger Sayle, "RasMol Version 2.6–Beta–2 Reference Manual," printed from www.umass.edu/microbio/rasmol/distrib/rasman.htm on Nov. 9, 1999.

Trifox, Inc., "CIS Developer's Notes," printout from 216.29.57.51/support/devnotes/devnotes.html on Nov. 5, 1998.

Trifox, Inc., "Company Information," printout from www.trifox.com/company/index.html on Nov. 3, 1999.

Trifox, Inc., "DesignVision (TRIMapp) Users Guide," Sep. 21, 1999, Campbell, CA.

Trifox, Inc., "Partner Solutions," printout from www.trifox.com/company/partners.html on Nov. 5, 1998.

Trifox, Inc., "Trifox, Inc. DesignVision White Paper," printout from www.trifox.com/wpapers/dvwp.html on Nov. 3, 1999.

Trifox, Inc., "TRIMpl Function Reference 5,0.3.1.12," Sep. 21, 1999, Campbell, CA. pp. 1–205.

Trifox, Inc., "TRIMreport Reportwriter," Sep. 9, 1999, Campbell, CA. pp. 1–81.

Trifox, Inc., "TRIMqmr Users Guide," Sep. 7, 1999, Campbell, CA. pp. 1–136.

* cited by examiner

FIG. 1

| FIG. 5A |
|---|
| FIG. 5B |

| MM 003766 AZ54431 SC [C10] | | | | | | | | |
|---|---|---|---|---|---|---|---|---|
| ACI | MG/KG | VEH | NO | TOX | CUR | MSTTX | MSTC | T-C MSTT |
| I | 640.000 | OIL | 5 | 5 | 0 | 3 | 6 | 6 0 |
| A | 160.000 | OIL | 5 | 5 | 0 | 0 | 6 | 7 13 |
| I | 40.00 | OIL | 5 | 0 | 0 | 0 | 6 | 6 12 |

| MM 003766 AZ54431 SC [B97] | | | | | | | | |
|---|---|---|---|---|---|---|---|---|
| ACI | MG/KG | VEH | NO | TOX | CUR | MSTTX | MSTC | T-C MSTT |

| MM 007332 AJ47404 SC [488] | | | | | | | | |
|---|---|---|---|---|---|---|---|---|
| ACI | MG/KG | VEH | NO | TOX | CUR | MSTTX | MSTC | T-C MSTT |
| I | 640.000 | OIL | 5 | 0 | 0 | 0 | 6 | 3 9 |
| I | 320.000 | OIL | 5 | 0 | 0 | 0 | 6 | 2 8 |
| I | 160.00 | OIL | 5 | 0 | 0 | 0 | 6 | 1 7 |
| I | 80.00 | OIL | 5 | 0 | 0 | 0 | 6 | 1 7 |
| I | 40.00 | OIL | 5 | 0 | 0 | 0 | 6 | 1 7 |
| I | 20.00 | OIL | 5 | 0 | 0 | 0 | 6 | 1 7 |

| MM 007332 AJ47404 SC [488] | | | | | | | | |
|---|---|---|---|---|---|---|---|---|
| ACI | MG/KG | VEH | NO | TOX | CUR | MSTTX | MSTC | T-C MSTT |
| I | 640.000 | OIL | 5 | 0 | 0 | 0 | 6 | 3 9 |
| I | 320.000 | OIL | 5 | 0 | 0 | 0 | 6 | 2 8 |
| I | 160.00 | OIL | 5 | 0 | 0 | 0 | 6 | 1 7 |
| I | 80.00 | OIL | 5 | 0 | 0 | 0 | 6 | 1 7 |
| I | 40.00 | OIL | 5 | 0 | 0 | 0 | 6 | 1 7 |
| I | 20.00 | OIL | 5 | 0 | 0 | 0 | 6 | 1 7 |

FIG. 5B

ACROBAT READER - [SRI847.PDF]
FILE EDIT VIEW TOOLS WINDOW HELP

ASSAY OF BULK 6-METHOXY-8 (6-DIETHYLAMINOHEXYLAMINO)LEPIDINE DIHYDROCHLORIDE, WR-6026AF, BK01845

REPORT NO. 847

2HCl

CH₃

NH(CH₂)₆N(C₂H₅)₂

CH₃O $C_{21}H_{33}N_3O \cdot 2HCl$      MW = 416.43

OBJECTIVE

THE OBJECTIVE OF THIS INVESTIGATION WAS TO IDENTIFY AND ASSAY THE BULK WR-6026AF MATERIAL.

PAGE 3 OF 18   100%   8.5 x 11 IN

FIG. 6

ACCESSSION SAMPLE [27 DEC 98]
FILE  EDIT  ACTION  QUERY  HELP

THOR
SMI [_____] WRNO [___] CAS [___] MF [___] TDT STATUS [___]
[QRY] [ASINEX] [CHEMEDIT] [RESETWIN] [DEPICT] [UPDCAS] [SIMILSRCH] MW [___]

INFORMIX                                                    ROW STATUS [___]
NAME     [_____]
SALT     [_]
WRNO     [___]        RECD      [___]       HAZARDS      [_____]
RN       [___]        QTYRECD   [___]       EPA          [_____]
SUBCUDE  [___]        QOH       [___]       COLOR        [_]
ICD      [_]          UNIT      [_]         STATE        [_____]
TDR      [_]          UNITDEF   [____]      SOLUBILITY   [_____]
SUBID    [_]          STORAGE   [___]       HYGROSCOPIC  [_____]
PGS      [_]          SHELF     [__]        MELTING POINT [_____]
CONTRACT [____]                             STABILITY    [_____]

[QRY]
[QBE] [QRYWIN] [APPROW] [RESETWIN] [COMMIT] [DS NOTES] [MAKE DS] [BAR CODE]

CHEMICAL INFORMATION SYSTEMS

This application claims priority from U.S. provisional Application Serial No. 60/107,690, filed Nov. 9, 1998, which is incorporated herein by reference in its entirety.

I. FIELD OF THE INVENTION

The invention relates to information systems that include chemical and biological information. Furthermore, the invention relates the contents of different databases such that an user is able to view a chemical structure of a chemical used in biological experiments, for example, in conducting research into potential chemical structures that may obtain a desired pharmaceutical result.

II. BACKGROUND OF THE INVENTION

Prior chemical information systems have been primarily text based and/or included only a portion of any one database of the present invention. Notwithstanding the usefulness of the above-described information systems, more efficient and complete systems are needed by the research field. Furthermore, the above-described information systems are difficult to understand and use without receiving a large amount of training.

III. SUMMARY OF THE INVENTION

The invention relates to a Chemical Information System (CIS) that provides a framework for three functions: 1) Chemistry—the storage of the chemical structures and other related chemical information for each compound, 2) Inventory—allowing users to request shipment of compound samples between the repository and remote test sites for the purposes of testing, and 3) Biology—the storage and coordination of all data generated from the biological testing of each compound. The chemical information system provides database management and communications support for the utilization of all chemistry, inventory, and biology information associated with an organization's drug development program.

FIG. 14 provides an overview block diagram and flowchart for the operation of the chemical information system The chemical information system is a graphical user interface preferably implemented as software. FIG. 1 shows that a selection is made from a Main Menu. An average user will most likely access the Biology Application, the Inventory Application, or the Chemistry Application. The Biology Application and the Chemistry Application are linked to allow the user to view chemical information regarding a particular sample located from a search in the Biology Application. If the user needs assistance, then the user may select the Help menu/option depending on where the user is within the chemical information system or the Data Dictionary providing information and definitions of various terms and acronyms in the chemical information system. The Utilities and the Data Entry menus are primarily related to administrative functions for the updating and analysis of the chemical information system. The Quit option is self-explanatory. As will be readily apparent to one of ordinary skill in the art, the user is able to backtrack out from the sub-menus to the Main Menu.

As will be readily apparent to one of ordinary skill in the art, a variety of programming languages could be used to implement the described chemical information system. Furthermore, the interface could take a variety of forms depending on current technologies.

The chemical information system as implemented preferably uses off-the-shelf software in addition to specific software created by the inventors to allow in part the off-the-shelf software to work together in a coherent system. The chemical information system allows the user to visually see the chemical structure for a particular chemical sample that has had a particular result without leaving the chemical information system.

An objective of the invention is to correlate and relate information contained in different databases to assist pharmaceutical researchers and chemists.

Another objective of the invention is to provide an easy system for use by researchers and other users.

Further features and advantages of the present invention, as well as the structure and operation of various embodiments of the present invention, are described in detail below with reference to the accompanying drawings.

IV. BRIEF DESCRIPTION OF THE DRAWINGS

The present invention is described with reference to the accompanying drawings. In the drawings, like reference numbers indicate identical or functionally similar elements or steps.

FIG. 1 illustrates a main interface.

FIG. 6 depicts a scanned image being shown in Acrobat Reader.

FIG. 7 illustrates the accession interface.

FIG. 9 illustrates the request sample interface.

FIG. 10 illustrates a latter shipping interface.

V. DETAILED DESCRIPTION OF THE INVENTION

Figure 1:
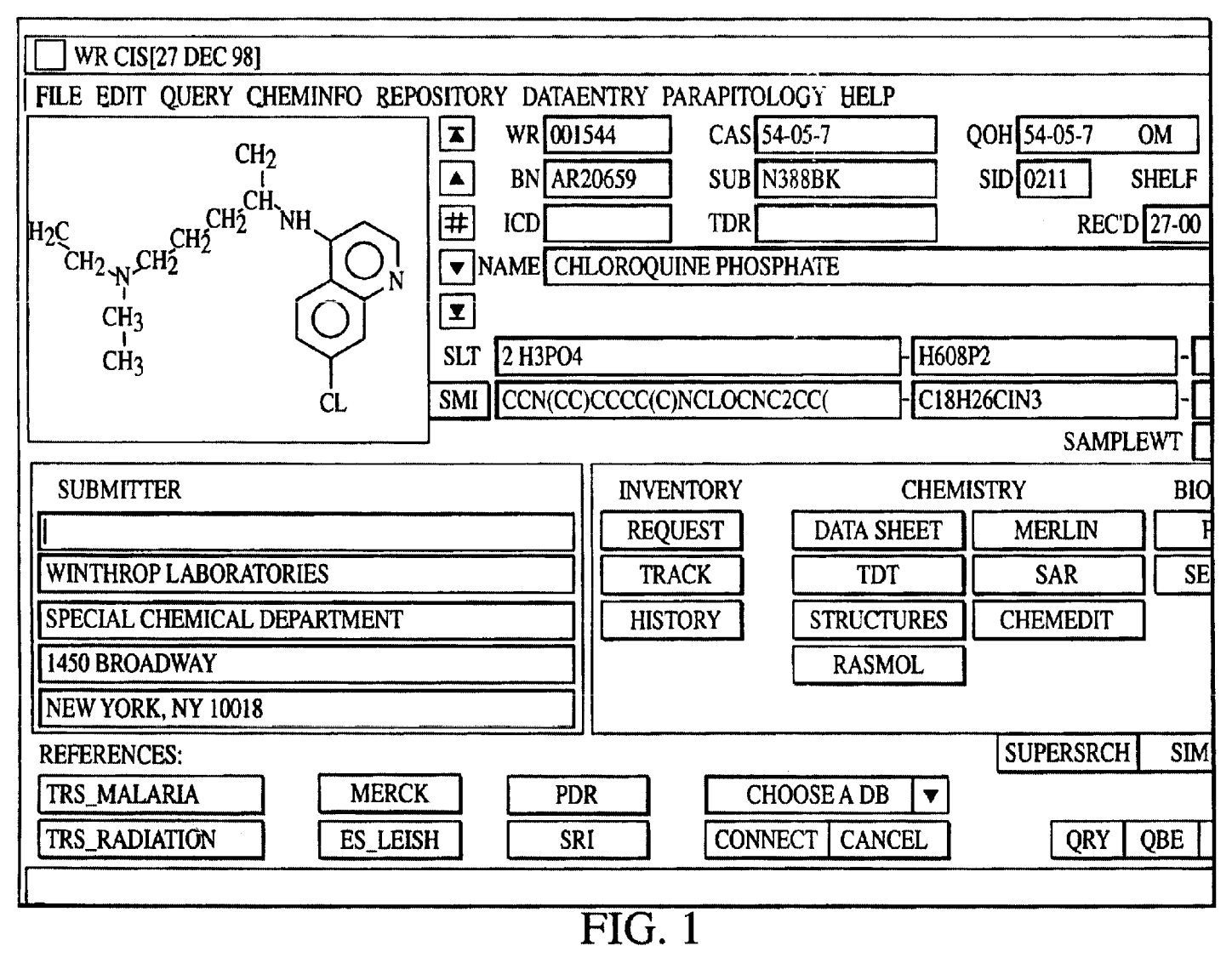

FIGS. 1–10 illustrate a preferred embodiment of the chemical information system of this invention. Preferably, the structural embodiment is accomplished using software. The invention integrates information that preferably includes chemical, biological, and inventory data, as illustrated in FIG. 1, from a variety of sources into displays that simplify the management of research and development activities of an organization. Preferably, the system relates the various sources of information such that when a record is updated in one area, that information is added and/or modified in the other sources of information that involve that record.

Figure 2:
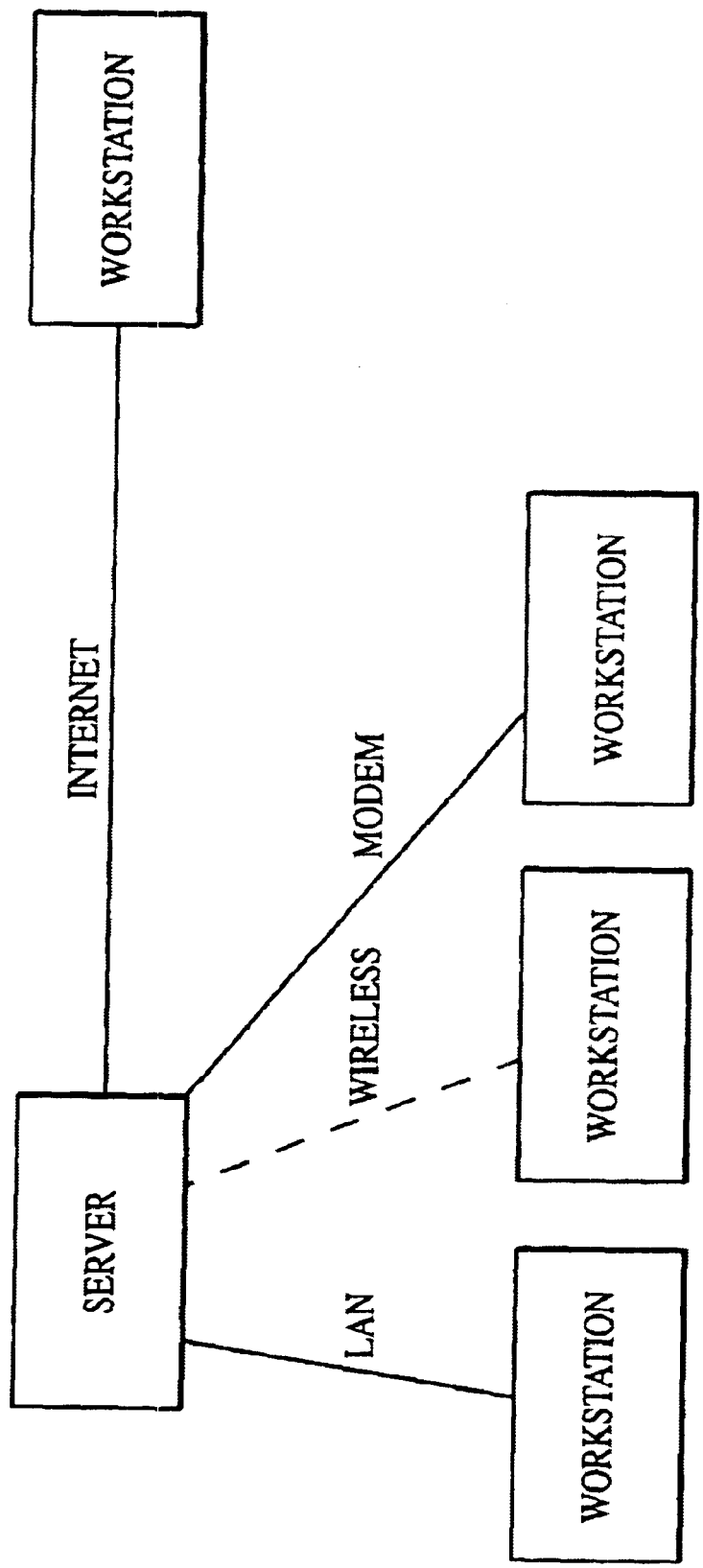
FIG. 2 depicts the system as a block diagram.
Figure 3:
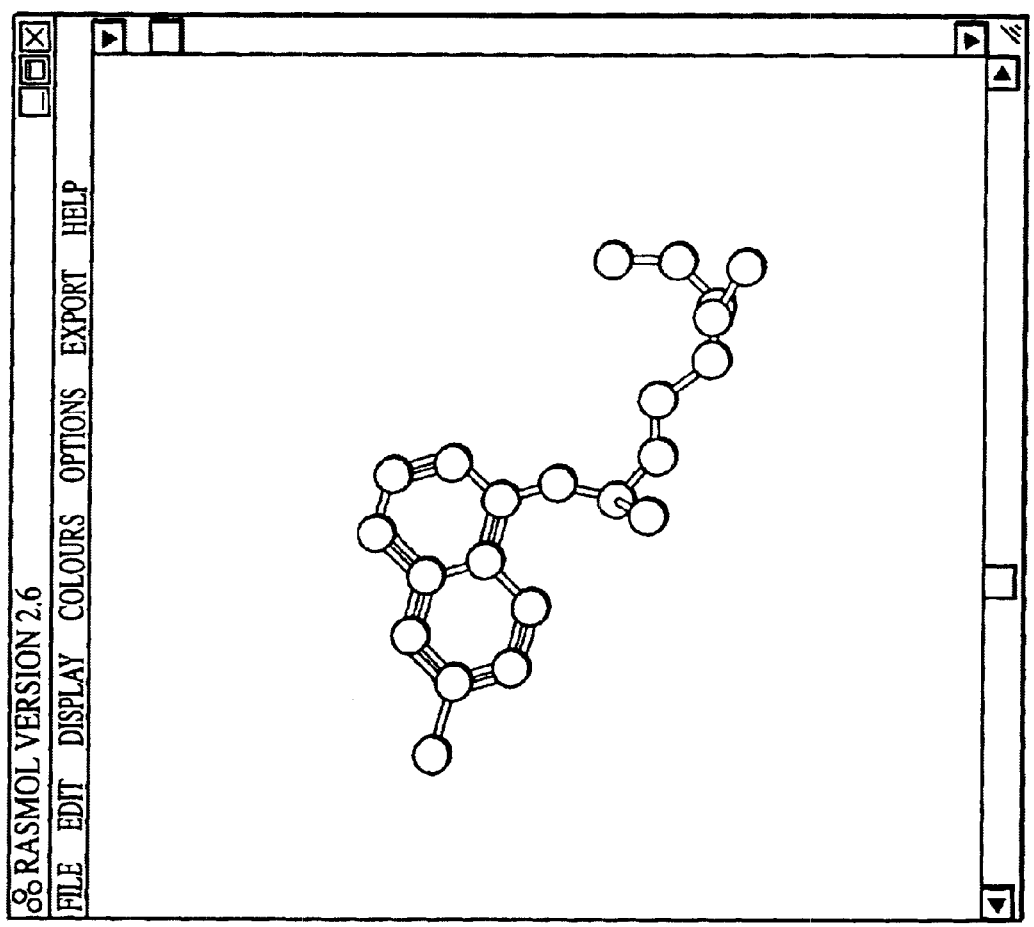
FIG. 3 illustrates a window showing a three-dimensional molecule depicted in FIG. 1.

The system preferably includes at least one server and multiple workstations/clients as illustrated in FIG. 2. Any reference to one server will include reference to a pool of servers unless explicitly stated otherwise. The connections between the server(s) and the workstations as shown in FIG. 2 may be accomplished over, for example, a cable, wiring, a wireless network, an infrared network, an optical network, a fiber optic network, or a PCS network. The connection between any one workstation and the server may be different than the connection between another workstation and that same server. The workstations preferably are fat clients, narrow clients, or Java machines, but may be any device capable of working with the server.

The server will house the software to interconnect a plurality of databases. The databases preferably cover chemistry, inventory, biology, test results, and reference materials. Preferably, each of these databases may be cross-referenced from each other to allow for all relevant data present to be correlated and presented in a graphical user interface (GUI) as shown in FIG. 1. Preferably, the graphical user interface will use a combination of pull down menus, textual fields, buttons, and graphical representations. Preferably, the interface will include an area to provide status information as to, for example, location within a set of search results and/or progress in communicating with a particular database. Furthermore, the graphical user interface preferably will include a help function to explain the use of discrete portions of the system ranging from textual description to search templates. Upon initialization of the software from any workstation, the software preferably will need to include in the respective initialization file the various necessary addresses for allowing communication with the server over the network or other connection.

The chemistry database preferably will include at least one of the following: two-dimensional and/or three-dimensional representations (FIG. 3)/structures of a chemical, a data sheet, and structural activity relationships.

The inventory database preferably will include at least one of the following: historical internal shipment information, status of a requested chemical, address information, and chemical particulars. The historical shipment information preferably will include who has requested a particular chemical, for what reason, and when. More particularly, the history will include all previous shipments of a particular compound to all test systems/experiments/laboratories. The status of a requested chemical preferably will allow for an individual to inquire with the system as to where along the request process the chemical present is. The address information preferably will include addresses of chemical providers (including past, present and potential) and laboratories to which chemical might be shipped. Preferably chemical particulars will be identification information and how much is on hand of any given sample. Preferably, access to particular functions for updating and/or revising the database will be limited based on needs of particular individuals for management of the chemical repository.

Figure 4:
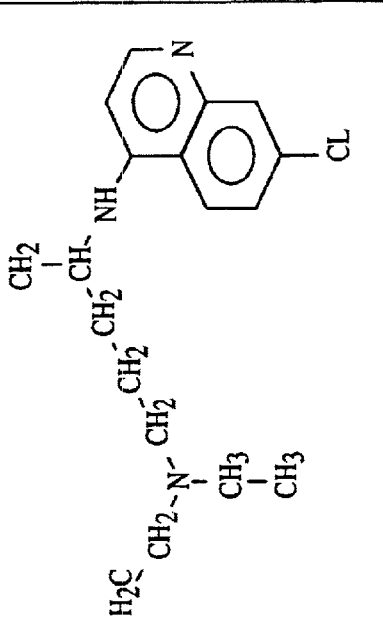
FIG. 4 depicts the main interface with biological information.
Figures 5, 5A:
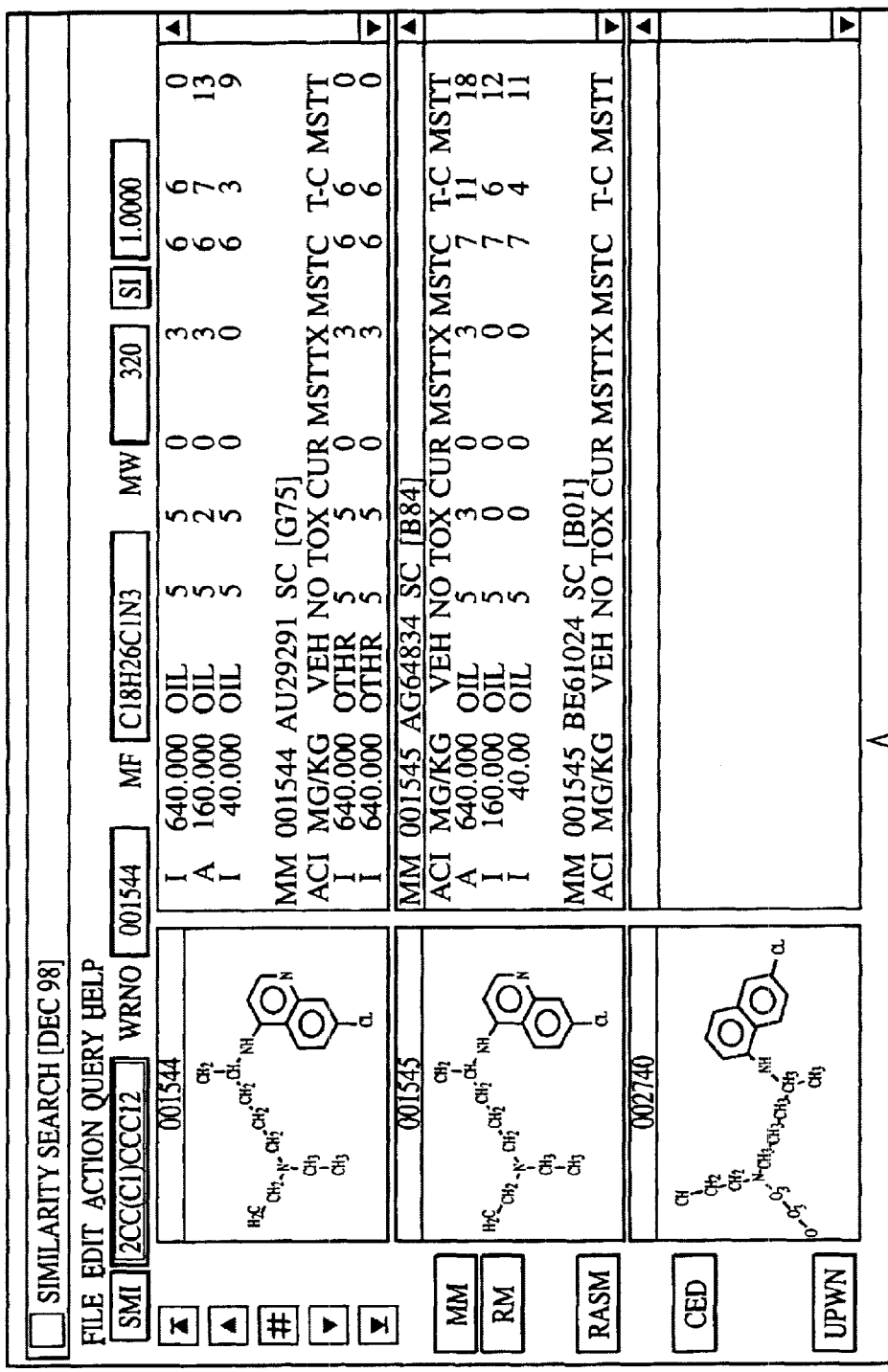
FIG. 5 illustrates an example of information from the chemistry and biology databases being displayed together.

The biology database preferable will include test data from past research results and other similar information as illustrated in FIGS. 4 and 5. Examples made be results from pharmaceutical testing on laboratory testing or drug trails. A further example of biological information from the In Vitro Malaria Screen experiments includes experimental protocol, parasite strain, and dose response data. Preferably, this type of data will appear in a child window. The biology databases preferably allow for importing of biological data into relational databases for later retrieval and display of multiple test systems with particular chemical structures as illustrated in FIG. 5.

Examples of reference materials that may be accessed in or via the system are Merck's Index, Physician's Desk Reference, submitted documents to the FDA, reports from other laboratories or organizations regarding particular chemicals as illustrated in FIG. 1.

Referring to FIG. 1, the main interface (or window) provides the starting point to the various functions within the system. Preferably, the main interface includes a summary of inventory and chemistry data for a particular sample, for example, a bottle. The main interface preferably also provides the user with access to the biology, chemistry, and inventory functions within the system along with reference materials and the Internet. Preferably, the main interface will begin in query mode.

The databases preferably are searchable by a variety of terms through a graphical interface relying upon boxes for entry of data that may include specific reference to a particular specimen by name, code/identification, or chemical structure. More particularly, the main interface preferably will include query fields for identification by sample number, chemical number (for example either organization or CAS identification), a subcode, and subid. Preferably, the search maybe performed using Boolean logic or other common search techniques such as those used for searching the Internet.

The system preferably will allow various software packages to function together to form a larger system. For example, the system may utilize any of the following in a variety of combinations: Daylight 4.62, Daylight Thor databases, Daylight Merlin pools, RasWin Molecular Graphics Windows Version 2.6 (FIG. 3), ChemDraw, ChemFinder, Adobe Acrobat (FIG. 6), and Netscape Navigator. Some of this software is used for displaying of information based on the type and nature of the information. For example, the RasWin Molecular Graphics Windows Version 2.6 preferably is used to display three-dimensional renditions of chemicals, while Adobe Acrobat and Netscape Navigator may be used to display scanned in images and html documents, respectively.

The method of operation of the system allows for the above-discussed databases to be linked to provide a more complete set of information regarding chemicals in a particular organization. Access to the various databases is prompted by triggers in response to entries made and buttons pressed by the user to retrieve information. The triggers preferably are miniprocedures to elicit particular information and/or perform particular functions within the disparate databases. The triggers preferably operate below a common styled graphical user interface that unites the look and feel of the information retrieved from the databases. These triggers facilitate the synchronization of the information in the databases so that when a change is made in one database the change is also made where appropriate and necessary in the related data present in the other databases.

A search preferably is accomplished by entering a search term either in a particular data field or an edit field. The particular data field will be attached to a certain type of data, which as mentioned previously may be an internal identification for a chemical or other alphanumeric representation of the chemical. The edit field preferably will allow for the use of a query template for a particular type of data. The query template may for example be search for a term having certain characteristics like less than, greater than, equal to, similar to, in a range/set, between x and y, not in a set, not equal to, like, is null, or not null. After entry of the search information, the user preferably will press a button or hit return to trigger the search in the relevant database(s) for information. The search results may be provided in the main interface or another window depending on the type of information. The information located from the search is displayed and the user may utilize buttons in the interface, a scroll bar, or a keyboard to scan/skim through the search results.

Preferably as illustrated in FIG. 1, the search result will include identification of the supplier of the chemical sample including name and address, an organization identifier (such as WRNO), a sample identifier (such as BN for bottle number), a name for the chemical sample, a SMILES representation, a two-dimensional graphical representation, quantity available for testing. Additional information might be location of the sample; inclusion of salts; molecular weights of the salt, the sample minus salt, and total; and miscellaneous subcodes and subidentifiers.

Preferably, the system will provide the ability to search using a tool called from the main interface. The tool preferably will allow the user to select the pool, the search field, the search type, the search value, and the number of hits to locate. The tool preferably will allow the search of external databases beyond those present within the system. After search results are returned, the user preferably will be able to select the type of presentation, for example, structure activity relationships (FIG. 5) or as a hypertext marked up language (html). The structure activity relationship preferably may also be called from the main interface. Preferably, the structure activity relationship will allow the respective biological information to display alongside the structure.

As shown in FIG. 1, once information is located after a search from the main interface, preferably, the user will be able to select additional types of display based on information in the chemistry database including the two-dimensional/three-dimensional representations and chemical data sheets discussed previously. The information preferably is accessible through at least one of a button on the main interface or a pull down menu, which in turn will activate a trigger to send particular data or retrieve particular data to a display function.

The main interface preferably will provide a gateway to view other materials and references relating to the located chemical. This preferably will be accomplished via the use of buttons, but may also be accomplished through a pull down menu. Preferably, only the materials and references with information relating to the particular/selected chemical will be able to be activated.

Preferably, two-dimensional chemical structures will display automatically as users browse through located compounds while in the main interface, i.e., while the main interface is the active window.

The system interfaces with the inventory database when registering new samples into, for example, a Thor database. Transactions preferably include TDT updates, inserts, and deletes.

The accession function is based on the 'one to many relationship' between structures in the chemical database and samples in the Bottle table of the relational database. The accession function is divided into two windows: a parent window called Thor that mediates transactions with Thor and a child window called Bottle that mediates transactions with the Bottle table. An example of this is FIG. 7. Depending on the type of transaction, the two windows can operate dependently or independently. The two windows are joined on WRNO, the structure number, and a query in one window will automatically update the other. The registration of a new compound requires the insertion of data in both the Thor and Bottle windows while the registration of substance without a structure involves the insertion of data into the Bottle table only. Finally, both Thor and Bottle are updated independently.

A new chemical substance preferably is added using an accession function of the system. Preferably, the accession function is called from a pull down menu under, for example, Repository Manager. The accession function preferably allows for queries, updates, registering new structures, registering new samples, registering a sample without a structure, registering samples from ASINEX, and logging work. Exemplary descriptions of the steps involved in performing each of these functions is discussed below with preferable button names indicate as "[name]" and LOV represents "list of values."

To query in the Thor window, hit [QRY] for query mode, enter values, and [QRY] to execute. SMILES, WRNO, and CAS will be retrieved from Thor with calculations for MF and MW. If [Depict] is toggled on, the structure will be displayed. Finally, the Informix window will be updated. To query the Informix window, focus on it with the mouse and hit [QRY],enter values, [QRY]. Data will be retrieved from the Bottle table and displayed in the Informix window before the Thor and Depict windows are updated.

The CAS field is the only field in the Thor window that can be updated. Query on SMI or WRNO to select a record from Thor and then enter or change its CAS number. Hit [UpdCAS] to update Thor. To update the Bottle table, focus on the Informix window and query to select a record. Edit the record and hit [Commit].

The first step to registering a new structure is to enter the SMILES from the keyboard or the clipboard and press [tab] to execute the SMI validation trigger. The USMILE will be generated and used to search Thor to determine if the structure has already been registered. If the structure is new, the last registered WRNO will be incremented and assigned to the WRNO fields in the Thor and Informix windows. The last registered BN will be incremented and assigned to the Informix window. Complete all fields in the Informix window with yellow backgrounds and press [Commit] to insert the new TDT into Thor and the new sample record into the Bottle table.

The first step in registering a new sample is to enter the SMILES from the keyboard or the clipboard and press [tab] to execute the SMI validation trigger. The USMILE will be generated and used to search Thor to determine if the structure has already been registered. If a TDT for the structure is found, it is assumed that the user wants to register a new sample. The last registered BN is incremented and assigned with the structure's WRNO and the SYSDATE to the Informix window. Complete all fields with a yellow background in the Informix window and press [Commit] to insert the new record for the sample into the Bottle table.

The first step in registering a sample without a structure is to focus on the Informix window and press LOV (=F11] to populate the Name, Salt, WRNO, BN and Rec'd fields automatically. Complete all fields with a yellow background and press [Commit] to insert the new record for the sample into the Bottle table. Unstructured substances are not registered in Thor.

The method to register samples from ASINEX is as follows. The [AsinEx] action button provides access to the catalog of organic compounds from AsinEx Ltd that is distributed by Daylight Chemical Information Systems as a Thor database. Pressing [AsinEx] prompts for an AsinEx number that is used to search Thor. If found, the SMILES, MF, MW, Name, Salt, subcode, subid, PGS, Rec'd, QtyRec'd, QOH, Unit, UnitDef, Hazards, Storage, and Shelf are displayed. By pressing [tab], Thor will be searched on the SMILES to determine if the structure is already registered and the WRNO and BN will be incremented for new structures and samples as appropriate.

During the use of accession function a log preferably is maintained automatically. The 'File/Print Log' option on the menu bar can be used to print completed transactions. This option prints the window list of the BOTTLE window to an HTML document. To select a log of accession transactions follow these steps: 1. focus on the BOTTLE window; 2. [QRY]; 3.Focus on the BN field; 4.[QBE] and choose: A.BN between 'A7' and 'A7'; 5.[QryWin] and substitute your BNs for 'A7' (i.e.) A.BN between 'BN00000' and 'BN00100'; 6.[QRY]; and 7.Select 'File/Print Log' on the menu bar.

The actions that preferably are allowed in the exemplary embodiment in the Thor window are read, update and insert to the Thor database. The MF and MW fields are calculated fields. The actions that preferably are allowed in the exemplary embodiment in the Informix window are read, update, insert and delete to the bottle table.

The query fields in the Thor window are SMI, organization number (WRNO) and CAS, while in the Informix window the query fields are bottle number (BN), subcode, ICD, TDR, and subid. The fields in the Informix window that are updateable are written to the data sheet html document only. These fields are for example solubility, hygroscopic, melting point and stability.

Figure 8:
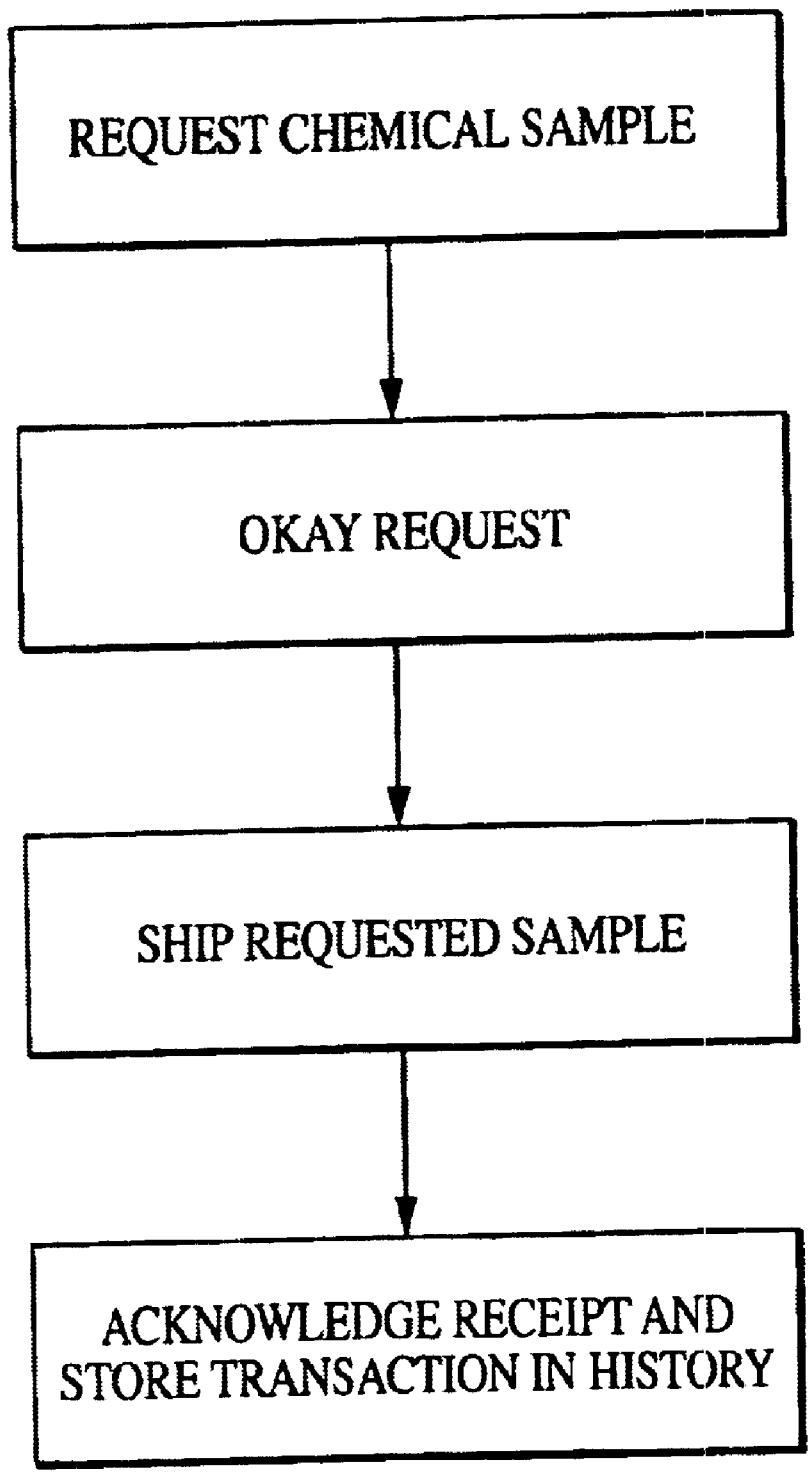
FIG. 8 depicts a block diagram illustrating the steps involved in requesting and receiving a chemical sample in the invention.

As shown in FIG. 8, the system preferably includes a process in which to request and receive chemical samples. The preferred method is 1) to have the investigator request a particular chemical sample, 2) repository manager sign off and okay the request, 3) the repository ship the chemical sample, and 4) an acknowledgment by the requestor.

Figures 9, 10:
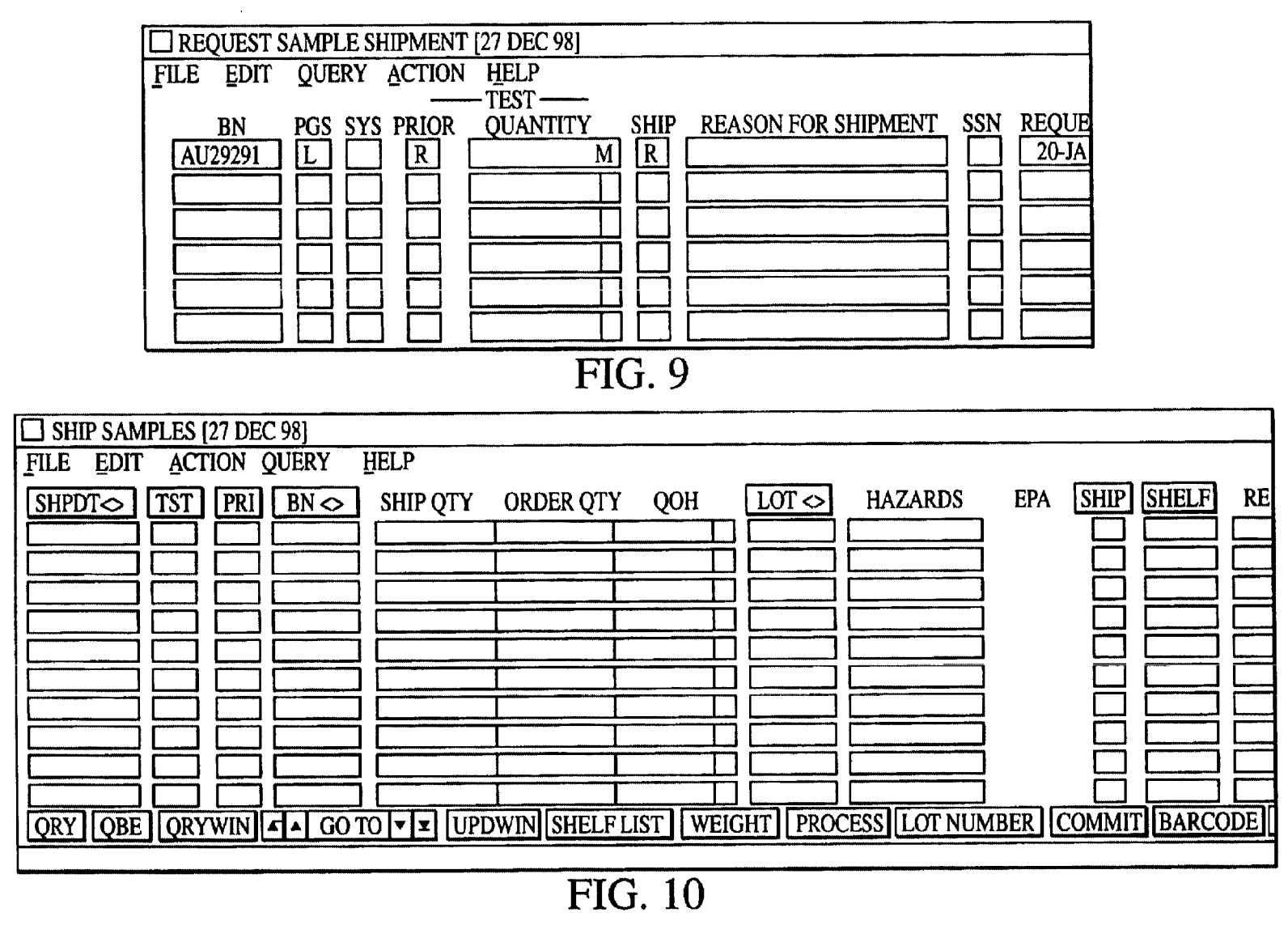

A sample is requested by the investigator/researcher preferably by having him/her select the function from the main interface. This will in turn trigger the system to display an order form. The requestor preferably will provide a personal identification, a bottle number, a test system (laboratory), experiment, and a basis for the request. An example is illustrated in FIG. 9. The personal identification may act as a security blanket to prevent false requests for chemicals. The bottle number preferably is provided if the request is the result of a search. The test system provides the shipping location for the chemical sample. The experiment will be included if this information will be of assistance for tracking and/or processing of the order. The system preferably will provide a list of test systems and experiments to select from for the user. The basis for the request ideally will provide an audit trail for latter reference if shipments are saved to a historical shipping file. Preferably the system will provide the option to duplicate the information for placement of a second shipment request of that same chemical sample for another experiment.

The next step is for the repository manager to approve requested shipments. Preferably, the system will include an option for the repository manager to select to initiate this step. The system preferably will provide a table including all the information entered in the requesting step. The repository manager preferably will be offered the choice to approve/disapprove all requests or some subset of all of the requests. An exemplary embodiment is as follows. To order the shipment of compounds the repository manager can select all samples in the Order Table without a request date by placing the cursor on the Order field and using the QBE utility: [QRY], [QBE], choose 'ORDDATE IS NULL', [QRY]. Records from the Order table will be sorted on by priority of shipping in descending order with subsorts on Test System. To learn more about the current sample and to depict its structure, press [UpdWins] to query the Start Window on the current BN in the Order Samples Window. Most fields can be updated from the keyboard or from LOV. Note that LOV in the Order and Request fields will paste SYSDATE into the field. A new record can be generated by pressing [DupRow] while a record can be marked for deletion with [DelRow]. Finally, a record can be updated, inserted or deleted by pressing [Commit].

The third step is for the repository to ship the chemical sample based on the request. An example is illustrated in FIG. 10.

The fourth step preferably is for some sort acknowledgment of receipt by the requester. Upon receipt the shipping record will be closed and preferably added to the historical shipment information for this particular chemical sample that was received. Preferably the historical shipment information will be searchable for any of the fields entered to place the initial request of the chemical sample.

An additional feature that may be added is the setting of the level of urgency of the request by the requestor. The level of urgency may in turn trigger an alarm for quicker review by the repository manager and also quicker shipment of the chemical sample. This additional feature is included in the following exemplary embodiments of shipping the requested chemical sample.

Selecting Data: To select data, press the [QRY] action button to enter query mode, enter your search string(s) in the available field(s), and press [QRY] again to execute the query. Only records with 'Order Dates' will be returned. To select orders without 'Ship Dates', focus on the ShipDT field, hit [QRY], [QBE], choose 'shipdate is null', [OK], and [QRY]. When entering a search string on LOT uses the '%' sign to retrieve multiple records. For example, 'TT001%' will return all records where LOT='TT001'.

Sorting Data: Retrieved data will be ordered by the 'Priority of Testing' with the 'Test First' samples at the top of the display. You can change the sort order by pressing any of the action buttons used as field labels. For example, if you want to order the data by shelf location, just push the button labeled Shelf.

Shelf List: The Shelf List is used to find the samples in the repository. First select the samples to process and then press the [Shelf] button on top of the Shelf field to sort the data by shelf location. Finally press the [Shelf List] button to display the list in the browser and print it locally or save it as an HTML document.

Navigating: In addition to the keyboard and the left mouse button, you can press the 'arrow' action buttons at the bottom of the display. The up/down arrows will move the cursor up/down one row. The up/down arrows with a bar will move the cursor to the top/bottom of the window list. To find a specific bottle number, press the [GoTo] button, enter the BN from the keyboard or a bar code, and press OK.

Processing Samples: To update the QOH press the [Process] action button. 1.The ship weight of the current row will be subtracted from the QOH. 2.The new QOH will be assigned to all rows where the BN equals the current BN. 3.When QOH goes to zero, the value in the shelf field will change to 'EMPTY'. 4.The system date will be entered into the Ship Date field.

Lot Numbers: Lot Numbers are used to manage the shipment of large numbers of samples to a Test System. The format of a lot number is 'CC999' with the two characters representing the Test System and the three digits representing sequenced numbers ranging from 001–999. Two additional numbers are used to manage lot numbers, Count (999) and Max (999). Max is the maximum number of samples per lot and the user assigns this number. Count is the sequential number assigned to each sample.

To assign a Lot Number, press the [Lot Number] button. If Lot Numbers are currently not used for the test system, the user will be given the choice to implement lot numbers. Lot numbers are generated, incremented and assigned automatically. When a lot is full, the user is given an Information Message, the current Lot Number is incremented (TS001–TS002) and the Count is reset (001). To stop the generation of Lot Numbers, don't press the [Lot Button].

Commit: Commit changes to the Order and Bottle Tables by pressing the Commit] action button.

Ship List: The Ship List is used by the shipper and receiver to document the contents of a package. First, select the samples to be shipped by selecting for a particular Ship Date (Focus on ShipDT field, [QRY], [QBE], select 'WHERE SHIPDATE='DDMONYY', [OK], [QryWin], substitute DDMONYY with your date, [OK], [QRY]). Press the [Tst] action button on top of the Test System field to order the window list by Test System. Press the [Ship List] action button to generate ship lists for each test system. The first test system will be displayed in the browser from which it can be printed. If there are ship lists to two or more Test Systems, the HTML shipping documents will be saved to the cache directory (i.e. TRIMhome\cache).

Ship Labels: Shipping labels can be printed from the Address Application on the Zebra Label Printer. First update all open windows by pressing the [UpdWins] action button at the bottom of the Ship Window. Then focus on the Address Window and press the [Label] action button.

Tab Delimited File: The Ship List can also be formatted into a 'Tab' delimited ASCII file by choosing 'Tab Delimited File' from 'File' on the menu bar. First select the samples to be shipped to a particular Test System. The file will be saved to the TRIMhome\cache directory.

Between the time a chemical sample is requested and then received, the system preferably will allow for the status of the request to be tracked. Preferably, the system will include a series of buttons for each of these described functions and capabilities on the main interface.

Figure 11:
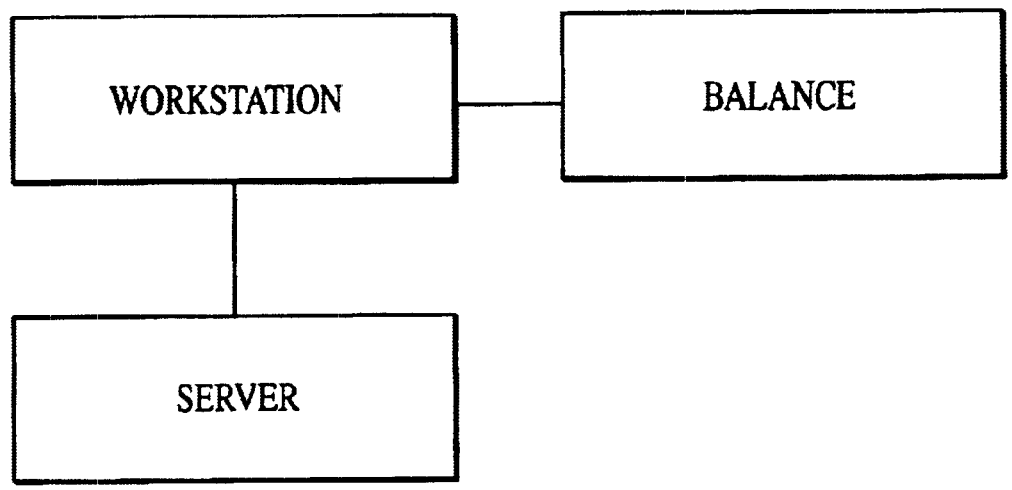
FIG. 11 depicts an alternative embodiment with a balance.

An alternative embodiment of the system, illustrated in FIG. 11, allows for the system to interact with scales to weigh different samples upon, for example, accession and shipment. A communication port in a workstation preferably is configured to exchange data with a balance, for example a Mettler/Toledo College B balance. The system preferably will include an option as either a button or a pull down menu to initiate communication with the balance.

The system preferably will have preset data fields for the port, baud rate, parity, bits, flow, command, and output file for receiving information from a particular balance connected to a particular workstation. This data preferably is set upon setup of the balance and the workstation. The port is for the communications port being used in the workstation, for example, com1, com2, com3, etc. The baud rate for the corn port may be 2400, 4800, 9600, 19200, 28800, etc. Parity is set as follows: 0 for no parity, 1 for odd, 2 for even, 3 for mark, and 4 for space. The bits per byte are set as, for example, 4, 5, 6, 7, or 8. Flow represents the flow control selected, for example, 0 represents hardware (DTR/CTS) and 1 represent Xon/Xoff. The outfile stores the data received from the balance.

The system preferably will call a routine to pass at least one parameter to the balance upon initiation of the procedure. The balance and the system preferably exchange data relating to the weight of the specimen.

An exemplary arrangement to illustrate this alternative embodiment is as follows. When the configuration parameters are established, they must be entered into wrcis.ini. The user is prompted for the serial port connected to the balance, baud rate, parity, bits per bite, flow protocol, balance command, and the filename to store the results returned from the balance. The user entries are stored in a file called c:\tmp\infile.ini. A 'C' program called TRIMhome\bin\scale.exe is called and infile.ini is passed as a parameter. Scale.exe sends the command to the balance and files its response in 'outfile', an environmental variable that stores the path/filename as defined in TRIMhome\lib\wrcis.ini. Finally, the balance application reads 'outfile' and displays the data in the result field.

The method for weighting a sample is as follows. Toggle up/down to the sample to be processed and weigh the sample by pressing the [Weigh] action button. If a balance has been installed, the following actions will occur. First, the computer/balance exchange will be established and the balance reset. Second, place the empty container on the scale tray and press the 'Tare Bar' on the balance. Third, add the amount of sample shown on the balance display and press the 'Tare Bar' again to transfer the weight to the SHIP field. Fourth, if the balance returns an error, it will be displayed on the status line.

Figure 12:
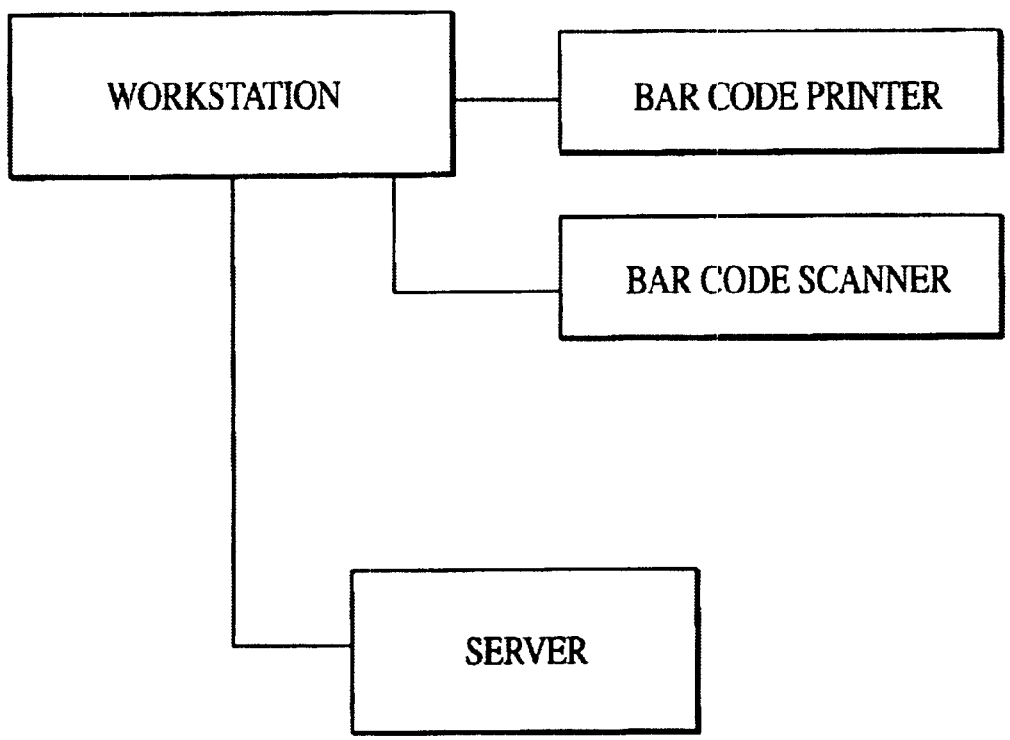
FIG. 12 illustrates a further alternative embodiment with bar code apparatus.
Figure 13:
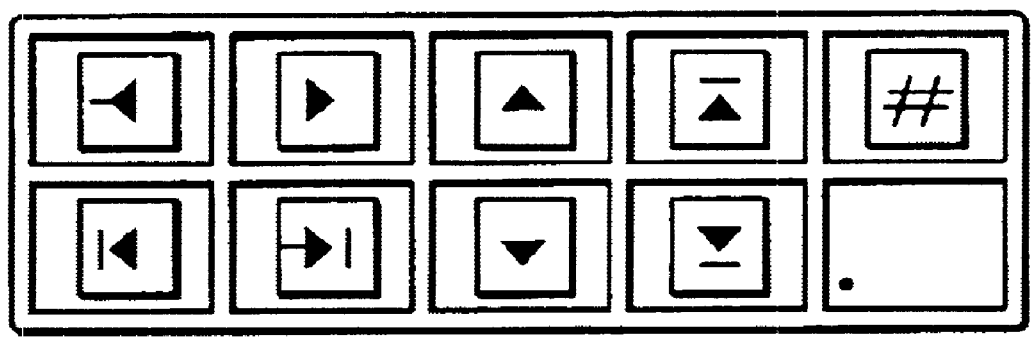
FIG. 13 depicts different buttons that might be used in the graphical user interfaces of this system.

Another alternative embodiment of the system, illustrated in FIG. 12, includes a bar code printer and bar code scanner for the handling of samples within, for example, a central repository of chemicals. An example of a bar code printer is the Blaster Advantage Desktop Bar Code Printer. This alternative embodiment should improve efficiencies in handling and in the future may allow for further automation of requesting process especially if combined with the alternative embodiment with a scale. A wand can be used to read bar code data into a field. To print a bottle label on the Blaster Advantage Printer with the bottle number and the quantity, move the cursor to the correct row and press the [Bar Code] button.

Preferably, the bar code printer will be used to print labels for new samples registered in the system, on bottles containing requested chemical samples, and for address labels for shipping boxes.

Another alternative embodiment is for the system to include for some functions pull down selection within the body of a window in contrast to a pull down menu from the header of a window. This is illustrated by the "Chose a DB" box with pull down arrow shown in FIG. 1.

A further alternative embodiment is for a continuous log to be maintained regarding communications with some or all of the databases that are a part of the system. This log may also provide an indication of the status of an operation, which will be informative when there is a delay in communication or access to the information external to the workstation.

A further alternative embodiment includes a data dictionary. The data dictionary preferably provides a list of field definitions for reference by the system. The list may be used to create and manage database tables.

A further alternative embodiment will allow users familiar with SQL to perform searches using that language. The system preferably then will pass the search requests directly to the databases capable of handling SQL searches.

The buttons discussed and referenced above in the exemplary embodiments have the following descriptions:

[AsinEx]: The AsinEx Action Button provides access to the catalog of organic compounds as described above in 'How It Works'.

[ChemEdit]: Opens a chemical editor to draw structures. Two editors are offered, ChemDraw and Java_GRINS. To use one of these editors, it must be installed on the client and registered in the client's wrcis.ini initialization file. The SMILES from the SMI field is automatically saved to the clipboard and can be pasted into the editor for use as a template. After editing the structure, its SMILES can be copied to the clipboard and pasted back to the SMI field in the Thor window. Remember that SMILES generated in ChemDraw are not USMILES. To generate USMILES, paste them into the SMI field and hit [tab].

[ResetWin]: Removes all data from the Thor and Informix windows.

[Depict]: Toggles on a window to display chemical structures using SMILES from the SMI field.

[UpdCAS]: Updates Thor with CAS number.

[SimilSrch]: Calls Merlin to run a similarity search using the displayed SMILES as an argument and projects the results in the browser.

[TDT]: Displays TDT for the displayed SMILES in the browser.

[AppRow]: Appends a blank record to the bottom of the Window List and automatically assigns WRNO, increments BN and Rec'd. After completing the data fields the appended record can be committed to the Bottle table.

[ResetWin]: Removes all data from the Thor and Informix windows.

[Commit]: Commits data from the screen display to the Bottle table and to Thor.

[DS Notes]: Opens an editor where the user can enter 'free text'. This text is printed at the bottom of the HTML Data Sheet Document, but it is not saved to the Bottle table.

[Make DS]: Formats all data from the display into an HTML datasheet and projects it in the client's browse. It can be printed locally from the browser. Once again, data in the Solubility, Hygroscopic, Melting Point, and Stability fields as well as the text from [DS Notes] are printed, but not saved to the Bottle Table.

[BarCode]: Prints a bar code label with BN, Hazard, Storage, and EPA data. The label is printed on the Blaster Advantage Printer.

[QRY]: The Query Action Button changes the application from normal mode to query mode. After entering values [QRY] is hit a second time to execute the query.

[QBE]: The 'Query by Example' Button displays templates of SQL predicates for the active field. The user selects one of them and the window closes. Multiple predicates can be selected on multiple fields. Finally, the user must edit the templates to enter the actual search values using an editor that is opened from the [QryWin] action. Finally, the query is executed by pressing [QRY] a second time.

[QryWin]: The Query Window Button opens an editor and displays the SQL predicate returned from the [QBE] action. The editor is used to replace the variable names in the SQL template with the actual values to be used in the database search.

Figure 14:
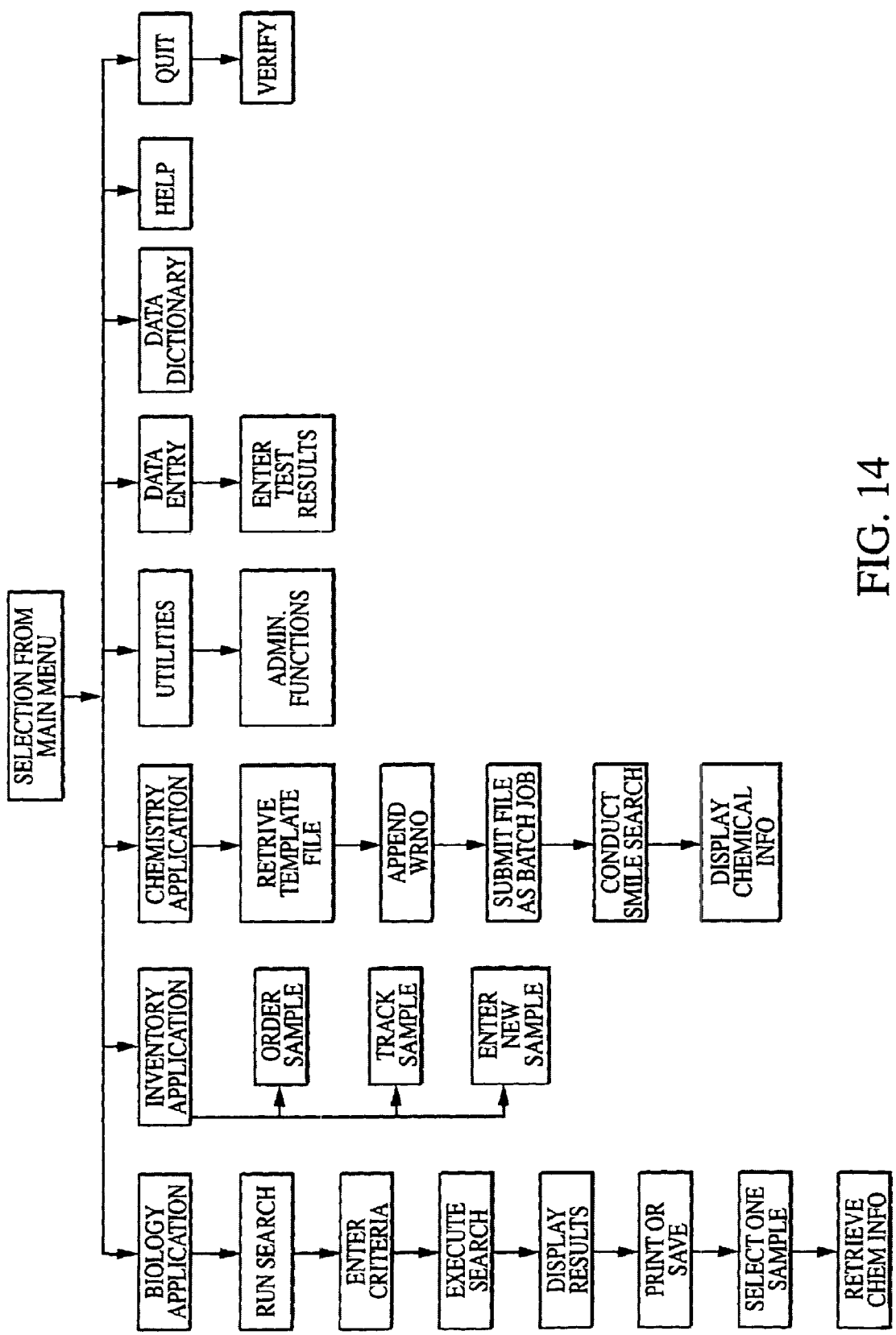
FIG. 14 illustrates a flowchart of an embodiment of this invention.

The next six buttons are illustrated, for example, as part of FIG. 14.

[UpdWins]: Executes the query trigger in all open windows using the BN of the Accession window as the join value.

[UpArrow with Bar]: Moves cursor to the first row in the window list.

[UpArrow]: Moves cursor to the preceding WRNO.

[#]: Prompts cursor to choose a row number and then moves the cursor to that row in the window list.

[DnArrow]: Moves cursor to the next WRNO.

[DnArrow with Bar]: Moves the cursor to the last row in the window list.

[DupRow]: Duplicates the and sets its row status to 'insert'. After editing the data fields the duplicate record can be inserted into the Bottle Table by hitting [Commit].

[DelRow]: Marks the active row for deletion and removes it from the window list. The marked record can be deleted from the database by hitting [Commit].

[Commit]: Commits data from the screen display to the Order table.

[OrdDate] will prompt the user to for an 'Order Date' and pastes this date into all Order fields in the window list.

[Hand Issue]: Formats the window list into a document authorizing the Repository Manager to ship samples to a test system that is not listed in the Address Table. Before using this utility, sort the window list on the BN field and then hit [Handissue]. The HandIssue document will appear in a text editor where the user can enter the 'Ship To:', 'Ship By:' and 'Special Instructions:' fields. Finally, the user is prompted for a filename and the HandIssue document is written in ASCII to the user's directory.

[TDT]: Searches THOR on the displayed SMILES and returns the Thor Data Tree as an HTML document that is displayed in the browser.

[Get DS]: Searches the BNPDF table in the relational database to determine if the Data Sheet for the current BN is available as a PDF file. If the BN is found, its network address is retrieved and used to get the PDF file from the Image Server. The Data Sheet is viewed in Adobe Acrobat Reader.

Those skilled in the art will appreciate that various adaptations and modifications of the above-described preferred embodiments can be configured without departing from the scope and spirit of the invention. Therefore, it is to be understood that, within the scope of the appended claims, the invention may be practiced other than as specifically described herein.

We claim:

1. A chemical information system comprising:

at least one server, a plurality of databases resident on said at least one server, said databases include a chemist database, a biology database, and an inventory database, at least two workstations in communication with said at least one server, a graphical user interface, said interface allowing searching, retrieving, synchronizing and correlating of information from at least two different databases, and a means for handling inventory including receiving orders, approving orders, and processing orders, said inventory handling means is in communication with said at least two workstations, a bar code reader in communication with said inventory handling means, a bar code printer in communication with said inventory handling means, and at least one balance; and wherein one of said at least two workstations is in communication with said at least one balance.

2. A The chemical information system comprising:

at least one server, a plurality of databases resident on said at least one server, said plurality of databases includes a chemistry database, a biology database having information relating to experiment results for at least some of the chemicals present within said chemistry database, and an inventory database, at least two workstations in communication with said at least one server, a graphical user interface, said interface allowing searching, retrieving, synchronizing and correlating of information from at least two different databases, and a means for handling inventory including receiving orders, approving orders, and processing orders, said inventory handling means is in communication with said at least two workstations, a bar code reader in communication with said inventory handling means, a bar code printer in communication with said inventory handling means, at least one balance; and wherein one of said at least two workstations is in communication with said at least one balance.

3. A method for handling inventory of chemicals comprising:

receiving an order for at least one chemical from an user, providing a list having at least one chemical order for approval, receiving instructions for approval or disapproval of at least one chemical order, when a chemical order has been disapproved, notifying the user of the disapproval, when a chemical order has been approved,
entering the chemical order for processing and shipment, and processing the chemical order for shipping; and wherein the processing step includes
receiving information relating to a chemical read in through a bar code reader,
verifying the chemical sample information matches the chemical order,
receiving a final weight for the amount of the chemical present upon a balance,
deducting the final weight for the amount of the chemical from available supply for the chemical,
creating a new record for the chemical order including an identifier and the user,
sending information relating to the chemical order including the identifier and the user to a bar code printer, and
notifying the user of shipment of the chemical order.

4. A data signal embodied in a carrier wave readable by a computing system, and encoding instructions for executing a process performing the method recited in claim 3.

5. A computer-readable medium having computer-executable instructions for the method recited in claim 3.

6. A chemical information system comprising:
a graphical user interface,
a biology database,
a chemistry database,
a biology application in communication with said graphical user interface and said biology database, said biology application having
means for processing a search request based upon entered criteria in said biology database,
means for displaying the results of the search in said graphical user interface, and
means for receiving a selection, retrieving information related to the selection from said biology database, and displaying the retrieved information in said graphical user interface,
an inventory application in communication with said biology application, said inventory application having
means for receiving orders,
means for tracking orders, and
means for entering new samples,
a chemistry application in communication with said graphical user interface and said chemistry database, said chemistry application having
means for conducting a SMILE search based upon entered criteria in said chemistry database, and
means for displaying chemical information located based upon the SMILE search in said graphical user interface; and
a data entry module in communication with said biology database, said data entry module having means for entering test results into said biology database.

7. The chemical information system according to claim 6, further comprising means for retrieving chemistry information relating to the selection received by said biology application from said chemistry database.

8. The chemical information system according to claim 6, further comprising means for retrieving biology information relating to the displayed chemical information from said biology database.

9. The chemical information system according to claim 6, wherein said ordering means includes
means for receiving an order for at least one chemical from an user,
means for providing a list having at least one chemical order for approval,
means for receiving instructions for approval or disapproval of at least one chemical order,
means for notifying the user of the disapproval when a chemical order has been disapproved,
means for entering the chemical order for processing and shipment when a chemical order has been approved, and
means for processing the chemical order for shipping when a chemical order has been approved.

10. The chemical information system according to claim 6, further comprising:
a balance in communication with said inventory application,
a bar code reader in communication with said inventory application, and
a bar code printer in communication with said inventory application.

* * * * *